United States Patent
Gilis et al.

(10) Patent No.: US 6,358,527 B1
(45) Date of Patent: *Mar. 19, 2002

(54) FAST-DISSOLVING GALANTHAMINE HYDROBROMIDE TABLET

(75) Inventors: Paul Marie Victor Gilis, Beerse; Valentin Florent Victor De Condé, Lommel, both of (BE)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

This patent is subject to a terminal disclaimer.

(21) Appl. No.: 09/585,122

(22) Filed: Jun. 1, 2000

Related U.S. Application Data

(63) Continuation of application No. 09/202,187, filed as application No. PCT/EP97/02986 on Jun. 6, 1997, now Pat. No. 6,099,863.

(30) Foreign Application Priority Data

Jun. 14, 1996 (EP) .............................................. 96201676

(51) Int. Cl.⁷ .............................. A61K 9/20; A61K 9/28
(52) U.S. Cl. ........................ 424/474; 424/465; 514/813; 514/879; 514/777; 514/781
(58) Field of Search .................................. 424/464, 465, 424/474, 475, 480, 482

(56) References Cited

U.S. PATENT DOCUMENTS

| | | | | |
|---|---|---|---|---|
| 4,663,318 A | * | 5/1987 | Davis et al. | 514/215 |
| 4,693,750 A | | 9/1987 | Bauer et al. | 106/163.1 |
| 5,633,238 A | | 5/1997 | Snorrason | 514/80 |
| 6,099,863 A | * | 8/2000 | Gillis et al. | 424/475 |
| 6,150,354 A | * | 11/2000 | Davis et al. | 514/215 |

FOREIGN PATENT DOCUMENTS

| | | |
|---|---|---|
| EP | 0 515 301 A2 | 11/1992 |
| EP | 0 515 302 A1 | 11/1992 |

* cited by examiner

*Primary Examiner*—James M. Spear
(74) *Attorney, Agent, or Firm*—Mary A. Appollina

(57) ABSTRACT

The present invention is concerned with a fast-dissolving tablet for oral administration comprising as an active ingredient a therapeutically effective amount of galanthamine hydrobromide (1:1) and a pharmaceutically acceptable carrier, characterized in that said carrier comprises a spray dried mixture of lactose monohydrate and microcrystalline cellulose (75:25) as a diluent, and a disintegrant; and with a direct compression process of preparing such fast-dissolving tablets.

6 Claims, No Drawings

FAST-DISSOLVING GALANTHAMINE HYDROBROMIDE TABLET

CROSS REFERENCE TO RELATED APPLICATIONS

This application is a continuation application of U.S. Ser. No. 09/202,187, U.S. Pat. No. 6,099,863 filed Dec. 9, 1998, which is a National Stage application under 35 U.S.C. §371 of PCT/EP97/02986 filed Jun. 6, 1997, which claims priority from EP 96.201.676.2, filed Jun. 14, 1996.

The present invention is concerned with a fast-dissolving tablet for oral administration comprising as an active ingredient a therapeutically effective amount of galanthamine hydrobromide (1:1) and a pharmaceutically acceptable carrier, characterized in that said carrier comprises a spray-dried mixture of lactose monohydrate and microcrystalline cellulose (75:25) as a diluent, and a disintegrant; and with a direct compression process of preparing such fast-dissolving tablets.

Galanthamine, a tertiary alkaloid, has been isolated from the bulbs of the Caucasian snowdrops *Galantanus woronowi* (Proskurnina, N. F. and Yakoleva, A. P. 1952, Alkaloids of *Galanthus woronowi* II. Isolation of a new alkaloid. (In Russian.) Zh. Obschchei Khim. (J. Gen. Chem.) 22, 1899–1902). It has also been isolated from the common snowdrop *Galanthus nivalis* (Boit, 1954). The chemical name of galanthamine is [4aS-(4aα, 6β, 8aR*)]-4a, 5, 9, 10, 11, 12-hexahydro-3-methoxy-11-methyl-6H-benzofuro[3a, 3, 2-ef][2]benzazepin-6ol; both the base compound and its hydrobromide are laevorotatory. Galanthamine is a well-known acetylcholinesterase inhibitor which is active at nicotinic receptor sites but not on muscarinic receptor sites. It is capable of passing the blood-brain barrier in humans, and presents no severe side effects in therapeutically effective dosages.

Galanthamine has been used extensively as a curare reversal agent in anaesthetic practice in Eastern bloc countries (cf. review by Paskow, 1986) and also experimentally in the West (cf. Bretagne and Valetta, 1965: Wislicki, 1967; Consanitis, 1971).

Galanthamine has been marketed by the Waldheim (Sanochemia Gruppe) as Nivalin™ in Germany and Austria since the 1970s for indications such as facial neuralgia.

The use of galanthamine or an analogue or a pharmaceutically acceptable acid addition salt thereof for the preparation of a medicament for treating Alzheimer's Dementia (AD) and related dementias has been described in EP-0,236,684 (U.S. Pat. No. 4,663,318). This patent only has a generic disclosure of possible dosage forms of galanthamine.

The use of galanthamine for treating alcoholism and the administration via a transdermal transport system (TTS) or patch is disclosed in EP-0,449,247. Similarly, the use of galanthamine in the treatment of nicotine dependence using administration via a transdermal transport system (TTS) or patch is disclosed in WO-94/16708.

A number of applications by E. Snorrason disclose the use of galanthamine, analogues thereof and pharmaceutically acceptable salts thereof for the preparation of medicaments for treating mania (U.S. Pat. No. 5,336,675), chronic fatigue syndrome (CFS) (EP-0,515,302; U.S. Pat. No. 5,312,817), and the negative effects of benzodiazepine treatment (EP-0,515,301). In these applications and patents, e.g. in U.S. Pat. No. 5,312,817, a number of specific tablet formulations of galanthamine hydrobromide are given. In particular, these formulations are as follows:

Composition of 1 tablet (60 mg) containing 1 mg galanthamine hydrobromide

| | |
|---|---|
| Galanthamine hydrobromide | 0.001 g |
| Calcium phosphate | 0.032 g |
| Lactose | 0.005 g |
| Wheat Starch | 0.0056 g |
| Microcrystalline Cellulose | 0.015 g |
| Talc | 0.0007 g |
| Magnesium Stearate | 0.0007 g |

Composition of 1 tablet (80 mg) containing 5 mg galantharmine hydrobromide; film-coat composition unknown [Nivalin™, Waldheim, Ltd, Vienna, Austria] (F 3)

| | |
|---|---|
| Galanthamine hydrobromide | 0.005 g |
| Calcium phosphate | 0.024 g |
| Lactose | 0.004 g |
| Wheat Starch | 0.004 g |
| Microcrystalline Cellulose | 0.04 g |
| Talc | 0.002 g |
| Magnesium Stearate | 0.001 g |

Composition of 1 tablet (120 mg) containing 10 mg galanthamine hydrobromide

| | |
|---|---|
| Galanthamine hydrobromide | 0.010 g |
| Lactose | 0.040 g |
| Wheat Starch | 0.0234 g |
| Microcrystalline Cellulose | 0.0374 g |
| Talc | 0.0036 g |
| Magnesium Stearate | 0.0012 g |
| Gelatin | 0.0044 g |

These tablet formulations can be prepared using wet granulation processes.

The dissolution (USP 23,<711> Dissolution, pp 1791–1793, Apparatus 2 (paddle, 50 rpm; 500 ml water or aqueous buffer at 37° C.)) of the commercially available Nivalin™ 5 mg film-coated tablet (F3) is as follows:

| Time (min) | Calculated concentration (% w/w) of the active dose | | | | |
|---|---|---|---|---|---|
| | H₂O | pH 4.5 USP | pH 6.5 USP | pH 7.5 USP | 0.1N HCl |
| 0 | 0.00 | 0.00 | 0.00 | 0.00 | 0.00 |
| 5 | 6.23 | 21.38 | 5.25 | 12.80 | 41.95 |
| 15 | 51.75 | 86.33 | 43.88 | 37.70 | 91.05 |
| 30 | 80.88 | 97.63 | 79.78 | 66.18 | 98.88 |
| 45 | 93.28 | 98.60 | 87.88 | 82.70 | 102.08 |
| 60 | 100.75 | 99.20 | 90.70 | 90.93 | 101.63 |

In order to obtain government approval to market a drug, one must not only show that the active ingredient has the stated activity and is safe to use, but it is also necessary to show that the formulation of the active ingredient will give a reproducible result in various patients. For example, in the case of solid formulations shaped as tablets, it is a prerequisite that the tablets disintegrate and dissolve within a particular period of time to a particular degree. In the present case, novel galanthamine hydrobromide tablets having a dissolution of at least 80% after 30 minutes (Q=80% after 30') (USP 23, <711> Dissolution, pp 1791–1793, Apparatus 2 (paddle, 50 rpm; 500 ml purified water at 37° C.)) are provided. Compliance with this dissolution specification is only met by using a particular diluent containing disintegrant, and a second disintegrant.

Thus the present invention relates to a tablet comprising as an active ingredient a therapeutically effective amount of galanthamine hydrobromide (1:1) and a pharmaceutically acceptable carrier, characterized in that said carrier comprises a spray-dried mixture of lactose monohydrate and microcrystalline cellulose (75:25) as a diluent, and a disintegrant. Said tablets have a dissolution of at least 80% after 30 minutes (Q=80% after 30') (USP 23, <711> Dissolution, pp 1791–1793, Apparatus 2 (paddle, 50 rpm)).

Initial experiments started out using either lactose anhydrous or lactose monohydrate as diluent, and either powdered cellulose or microcrystalline cellulose as disintegrant (see tablet formulations F1 and F2 in the Experimental Part). A particular problem which occurred during feeding the dry blend into the tablet press for direct compression, was segregation of the tablet excipients, thus causing the tablets to have a variable composition. In addition, the tablets formulations F1 and F2 did not comply at Stage 1 with the dissolution specification of Q=80% after 30'. In order to solve the percieved problems, the diluent was substituted for a spray-dried mixture of lactose monohydrate and microcrystalline cellulose (75:25), commercially available as Microcelac™. In addition to having a reduced tendency to segregate during feeding into the tablet press, the dry blend comprising the above diluent was further found to have excellent rheological properties (flowability), as well as to be easily miscible with the active ingredient and other tablet excipients. The dissolution specification was not met, however, unless a disintegrant having a large coefficient of expansion was employed, more in particular, if an insoluble or poorly soluble cross-linked polymer such as, for example, crospolyvidone or croscarmellose was employed. The amount of said disintegrants in the fast-dissolving tablets according to the present invention conveniently ranges from about 3 to about 8% (w/w), preferably about 5% (w/w).

In order to make the blending and the direct compression processes easier to perform, the carrier further comprises a glidant and a lubricant. Preferably, the glidant is colloidal anhydrous silica and the lubricant is magnesium stearate. In the initial experiments (see F1 and F2), talc was used as a glidant and sodium lauryl sulphate as a wetting agent/lubricant. The former was found to affect the dissolution properties of the tablets adversely (retarding the dissolution of the active ingredient) and the latter was found to be entirely superfluous and easy to omit from the tablet formulation.

Fast-dissolving tablets according to the present invention comprise by weight based on the total weight of the tablet core:
(a) from 2 to 10% galanthamine hydrobromide (1:1);
(b) from 83 to 93% spray-dried mixture of lactose monohydrate and microcrystalline cellulose (75:25);
(c) from 0.1 to 0.4% glidant;
(d) from 3 to 8% insoluble crosslinked polymeric disintegrant; and
(e) from 0.2 to 1% lubricant.
In particular, the tablets comprise:
(a) about 2 to 10% galanthamine hydrobrornide (1:1);
(b) about 83 to 93% spray-dried mixture of lactose monohydrate and microcrystalline cellulose (75:25);
(c) about 0.2% colloidal anhydrous silica;
(d) about 5% crospolyvidone; and
(e) about 0.5% magnesium stearate.

The fast-dissolving galanthamine hydrobromide (1:1) tablets according to the present invention may in addition include other optional excipients such as, for example, flavors, sweeteners and colors.

Tablets of galanthamine hydrobromide (1:1) are conveniently film-coated following art-known coating procedures. Film-coated tablets are easier to swallow than uncoated tablet cores, are usually easier to distinguish from other tablets—in particular when the film-coat contains a dye or a pigment—, and may furthermore have an improved stability (shelf-life). In the instant case, a mixture comprising a film-forming polymer and a plasticizer, in particular hydroxypropyl methylcellulose and a polyethylene glycol, e.g. macrogol 6000, may be employed for film-coating tablet cores as described hereinbefore. Of particular importance in the case of fast-dissolving tablets, is the requirement that the film-coat should not adversely affect the disintegration and dissolution of the active ingredient from the tablet. Therefore, the weight of the film-coat conveniently is in the range of 3 to 8%, particularly 4 to 7.5%, of the uncoated tablet core. As illustrated in the experimental part both the uncoated tablet cores and the film-coated tablets according to the present invention (F5, F6, F7) both comply with the dissolution requirement of Q=80% after 30' (USP).

The tablets according to the present invention are suitable as unit dose forms for oral administration to patients in need of galanthamine therapy. The tablets conveniently comprise from 2 to 20 mg galanthamine (2.563 to 25.63 mg galanthamine hydro-bromide (1:1)), in particular from 4 to 16 mg galanthamine (5.026 to 20.506 mg galanthamine hydrobromide (1:1)). They are best administered three times daily (t.i.d), approximately every eight hours, or two times daily (b.i.d), approximately every 12 hours, as these dosage regimens give therapeutic plasma levels of the active ingredient throughout the day.

The present invention is also concerned with a process of preparing fast-dissolving galanthamine hydrobromide (1:1) tablets, comprising the steps of:
(i) dry blending the active ingredient, the disintegrant and the optional glidant with the diluent;
(ii) optionally mixing the lubricant with the mixture obtained in step (i);
(iii) compressing the mixture obtained in step (i) or in step (ii) in the dry state into a tablet; and
(iv) optionally film-coating the tablet obtained in step (iii).

The dry blending can conveniently be performed in a planetary mixer; the direct compression on a tablet press; and the film-coating in a coating pan.

EXPERIMENTAL PART

EXAMPLE 1

Direct Compression Tablet Formulation (F1)
Ingredients

| | |
|---|---|
| galanthamine hydrobromide | 5 mg |
| lactose (anhydrous) | 70 mg |
| powdered cellulose | 19 mg |
| talc | 4 mg |
| sodium lauryl sulphate | 1 mg |
| colloidal anhydrous silica | 0.5 mg |
| magnesium stearate | 0.5 mg |
| total weight | 100 mg |

Preparation

The ingredients were intimately mixed in a planetary mixer and compressed in a tabletting machine, thus preparing tablets of 100 mg each.

EXAMPLE 2
Direct Compression Film-coated Tablet Formulation (F2)
Ingredients

| | |
|---|---|
| galanthamine hydrobromide | 5.13 mg |
| | (4 mg galanthamine) |
| lactose monohydrate | 55.11 mg |
| microcrystalline cellulose | 15.2 mg |
| talc | 3.2 mg |
| sodium lauryl sulphate | 0.8 mg |
| colloidal anhydrous silica | 0.16 mg |
| magnesium stearate | 0.4 mg |
| core weight | 80 mg |
| hypromellose 2910 5 mPa s | 1.8 mg |
| talc | 0.8 mg |
| titanium dioxide (E 171) | 0.1 mg |
| Macrogol 6000 | 0.3 mg |
| purified water* | 17 mg |
| film-coated weight | 3 mg |
| total weight | 83 mg |

*This component is not present in the final product.

Preparation

The ingredients were intimately mixed in a planetary mixer and compressed in a tabletting machine, thus preparing tablets of 80 mg each. The tablet cores were then film-coated in a coating pan.

EXAMPLE 3
Direct Compression Film-coated Tablet Formulation (F5)
Ingredients

| | |
|---|---|
| galanthamine hydrobromide | 5.126 mg |
| | (4 mg galanthamine) |
| spray-dried mixture of lactose monohydrate and microcrystalline cellulose (75:25) | 221.194 mg |
| crospolyvidone | 12 mg |
| colloidal anhydrous silica | 0.48 mg |
| magnesium stearate | 1.2 mg |
| core total weight | 240 mg |
| hypromellose 2910 5 mPa · s | 5.4 mg |
| talc | 2.4 mg |
| titanium dioxide (E 171) | 0.3 mg |
| Macrogol 6000 | 0.9 mg |
| purified water* | 51 mg |
| film-coat weight | 9 mg |
| total weight | 249 mg |

*This component is not present in the final product.

Preparation

The ingredients were intimately mixed in a planetary mixer and compressed in a tabletting machine, thus preparing tablets of 240 mg each. The tablet cores were then film-coated in a coating pan.

EXAMPLE 4
Direct Compression Film-coated Tablet Formulation (F6)
Ingredients

| | |
|---|---|
| galanthamine hydrobromide | 23.069 mg |
| | (18 mg galanthamine) |
| spray-dried mixture of lactose monohydrate and microcrystalline cellulose (75:25) | 203.251 mg |
| crospolyvidone | 12 mg |
| colloidal anhydrous silica | 0.48 mg |
| magnesium stearate | 1.2 mg |
| core total weight | 240 mg |
| hypromellose 2910 5 mPa · s | 5.4 mg |
| talc | 2.4 mg |
| titanium dioxide (E 171) | 0.3 mg |
| Macrogol 6000 | 0.9 mg |
| purified water* | 51 mg |
| film-coat weight | 9 mg |
| total weight | 249 mg |

*This component is not present in the final product.

Preparation

The ingredients were intimately mixed in a planetary mixer and compressed in a tabletting machine, thus preparing tablets of 240 mg each. The tablet cores were then film-coated in a coating pan.

EXAMPLE 5
Direct Compression Film-coated Tablet Formulations of Various Strength (F7a, F7b, F7c, F7d)

| Ingredients (in mg unless indicated otherwise): | F7a | F7b | F7c | F7d |
|---|---|---|---|---|
| galanthamine hydrobromide | 5.126 | 10.253 | 15.379 | 20.506 |
| (galanthamine) | (4) | (8) | (12) | (16) |
| spray-dried mixture of lactose monohydrate and microcrystalline cellulose (75:25) | 51.454 | 102.907 | 154.361 | 205.814 |
| crospolyvidone | 3 | 6 | 9 | 12 |
| colloidal anhydrous silica | 0.12 | 0.24 | 0.36 | 0.48 |
| magnesium stearate | 0.3 | 0.6 | 0.9 | 1.2 |
| core total weight | 60 | 120 | 180 | 240 |
| hypromellose 2910 5 mPa · s | 2.5 | 4 | 5 | 6 |
| propylene glycol (μl) | 0.603 | 0.965 | 1.207 | 1.448 |
| talc | 0.5 | 0.8 | 1 | 1.2 |
| titanium dioxide (E 171) | 0.75 | 1.2 | 1.5 | 1.8 |
| colorant(s) | 0.0032 | 0.013 | 0.505 | 0.130 |
| purified water* | 26.875 | 43 | 53.75 | 64.5 |
| film-coat weight | 4.3562 | 6.978 | 9.212 | 10.578 |
| total weight | 64.3562 | 126.978 | 189.212 | 250.578 |

*This component is not present in the final product.

Preparation

The ingredients were intimately mixed in a planetary mixer and compressed in a tabletting machine, thus preparing tablets of 60, 120, 180. and 240 mg. The tablet cores were then film-coated in a coating pan.

EXAMPLE 6

Comparative in-vitro dissolutions studies were performed on tablet formulations F1, F2, F5 (uncoated), F5 (film-coated), F6 (uncoated), F6 (film-coated) and F7a–d (film-coated). The medium was 500 ml of purified water at 37° C. in Apparatus 2 (USP 23, <711> Dissolution, pp. 1791–1793) (paddle, 50 rpm).

The following results were obtained:

| Time (min) | sample 1 | sample 2 | sample 3 | sample 4 | sample 5 | sample 6 | average |
|---|---|---|---|---|---|---|---|
| *F1* | | | | | | | |
| 0 | 0.00 | 0.00 | 0.00 | 0.00 | 0.00 | 0.00 | 0.00 |
| 5 | 77.85 | 59.10 | 72.40 | 74.48 | 76.23 | 61.35 | 70.23 |
| 15 | 87.33 | 78.88 | 86.73 | 83.40 | 89.08 | 76.33 | 83.62 |
| 30 | 90.98 | 84.15 | 88.40 | 87.43 | 91.78 | 82.20 | 87.49 |
| 45 | 92.78 | 87.28 | 90.30 | 89.83 | 93.30 | 85.83 | 89.88 |
| 60 | 93.58 | 88.95 | 91.00 | 92.35 | 96.35 | 89.83 | 92.01 |
| *F2* | | | | | | | |
| 0 | 0.00 | 0.00 | 0.00 | 0.00 | 0.00 | 0.00 | 0.00 |
| 5 | 34.48 | 24.42 | 33.92 | 37.35 | 33.67 | 33.33 | 32.86 |
| 15 | 85.23 | 75.32 | 79.39 | 85.23 | 84.26 | 73.93 | 80.56 |
| 30 | 90.55 | 84.99 | 87.31 | 90.30 | 90.64 | 83.11 | 87.82 |
| 45 | 92.84 | 88.89 | 90.45 | 92.47 | 93.49 | 88.38 | 91.09 |
| 60 | 94.40 | 90.69 | 92.28 | 93.91 | 94.62 | 89.74 | 92.60 |
| *F5 uncoated* | | | | | | | |
| 0 | 0.00 | 0.00 | 0.00 | 0.00 | 0.00 | 0.00 | 0.00 |
| 5 | 95.59 | 96.71 | 95.10 | 96.63 | 95.81 | 96.85 | 96.11 |
| 15 | 96.15 | 97.22 | 97.37 | 97.29 | 97.27 | 97.39 | 97.11 |
| 30 | 97.46 | 97.27 | 97.49 | 97.56 | 97.66 | 97.68 | 97.52 |
| 45 | 98.10 | 97.51 | 97.68 | 97.73 | 98.12 | 98.27 | 97.90 |
| 60 | 98.17 | 97.59 | 97.61 | 98.12 | 98.00 | 98.29 | 97.96 |
| *F5 film-coated* | | | | | | | |
| 0 | 0.00 | 0.00 | 0.00 | 0.00 | 0.00 | 0.00 | 0.00 |
| 5 | 86.27 | 81.08 | 89.37 | 87.81 | 92.95 | 86.93 | 87.40 |
| 15 | 92.76 | 93.29 | 92.90 | 93.34 | 97.46 | 93.27 | 93.84 |
| 30 | 97.27 | 96.24 | 95.07 | 95.20 | 98.05 | 94.61 | 96.07 |
| 45 | 98.12 | 97.51 | 96.27 | 96.63 | 98.20 | 95.68 | 97.07 |
| 60 | 98.05 | 97.66 | 96.49 | 96.66 | 98.22 | 96.61 | 97.28 |
| *F6 uncoated* | | | | | | | |
| 0 | 0.00 | 0.00 | 0.00 | 0.00 | 0.00 | 0.00 | 0.00 |
| 5 | 94.02 | 94.33 | 93.18 | 93.59 | 95.13 | 93.29 | 93.92 |
| 15 | 97.17 | 97.08 | 97.84 | 97.34 | 97.82 | 97.47 | 97.45 |
| 30 | 97.49 | 97.64 | 98.53 | 98.03 | 98.68 | 97.62 | 98.00 |
| 45 | 98.12 | 98.34 | 98.92 | 98.36 | 99.46 | 98.21 | 98.57 |
| 60 | 98.53 | 98.38 | 99.61 | 100.09 | 100.55 | 98.40 | 99.26 |
| *F6 film-coated* | | | | | | | |
| 0 | 0.00 | 0.00 | 0.00 | 0.00 | 0.00 | 0.00 | 0.00 |
| 5 | 94.61 | 77.70 | 95.63 | 90.51 | 83.90 | 78.94 | 86.88 |
| 15 | 98.14 | 96.93 | 99.81 | 97.32 | 96.25 | 95.86 | 97.39 |
| 30 | 98.81 | 99.05 | 100.61 | 99.51 | 99.29 | 97.97 | 99.21 |
| 45 | 99.74 | 99.61 | 100.70 | 99.59 | 100.13 | 99.90 | 99.95 |
| 60 | 100.24 | 100.76 | 100.74 | 100.13 | 100.52 | 100.57 | 100.50 |
| *F7a film-coated* | | | | | | | |
| 0 | 0.00 | 0.00 | 0.00 | 0.00 | 0.00 | 0.00 | 0.00 |
| 10 | 79.2 | 83.9 | 87.1 | 86.4 | 81.0 | 84.7 | 83.7 |
| 20 | 88.3 | 93 | 94.5 | 93.4 | 89.8 | 93.7 | 92.1 |
| 30 | 91.9 | 96.0 | 96.5 | 95.9 | 92.8 | 96.2 | 94.9 |
| 45 | 93.5 | 97.5 | 97.1 | 97.2 | 94.5 | 97.8 | 96.3 |
| 60 | 94.0 | 98.8 | 97.9 | 98.0 | 95.4 | 98.7 | 97.1 |
| *F7b film-coated* | | | | | | | |
| 0 | 0.00 | 0.00 | 0.00 | 0.00 | 0.00 | 0.00 | 0.00 |
| 10 | 77.2 | 73.0 | 83.3 | 82.3 | 82.1 | 80.7 | 79.8 |
| 20 | 88.1 | 86.4 | 91.6 | 91.2 | 93.9 | 90.6 | 90.3 |
| 30 | 92.4 | 91.1 | 93.9 | 93.4 | 96.4 | 93.7 | 93.5 |
| 45 | 94.8 | 93.3 | 94.7 | 94.9 | 98.2 | 95.0 | 95.1 |
| 60 | 96.1 | 95.2 | 95.7 | 95.7 | 99.2 | 95.9 | 96.3 |
| *F7c film-coated* | | | | | | | |
| 0 | 0.00 | 0.00 | 0.00 | 0.00 | 0.00 | 0.00 | 0.00 |
| 10 | 85.9 | 92.1 | 93.4 | 92.0 | 95.8 | 93.2 | 92.1 |
| 20 | 96.0 | 98.3 | 98.3 | 97.8 | 100.2 | 99.7 | 98.4 |
| 30 | 99.6 | 99.5 | 98.6 | 98.6 | 100.4 | 100.4 | 99.5 |
| 45 | 101.3 | 100.2 | 98.8 | 99.1 | 100.8 | 101.0 | 100.2 |
| 60 | 102.0 | 100.5 | 99.0 | 99.2 | 100.8 | 101.0 | 100.4 |
| *F7d film-coated* | | | | | | | |
| 0 | 0.00 | 0.00 | 0.00 | 0.00 | 0.00 | 0.00 | 0.00 |
| 10 | 70.1 | 82.1 | 77.8 | 81.6 | 82.6 | 79.9 | 79.0 |
| 20 | 86.0 | 95.0 | 90.6 | 93.3 | 90.8 | 92.6 | 91.4 |
| 30 | 94.1 | 99.0 | 94.4 | 96.9 | 94.0 | 97.1 | 95.9 |
| 45 | 98.1 | 101.8 | 99.5 | 98.5 | 95.7 | 99.2 | 98.8 |
| 60 | 102.3 | 102.1 | 98.2 | 99.4 | 96.5 | 100.3 | 99.8 |

Neither of F1 and F2 comply at stage 1 with the dissolution specification Q=80% at 30 minutes; both F5 (uncoated), F5 (film-coated), F6 (uncoated), F6 (film-coated) and F7a–d (film-coated) comply at stage 1 with the dissolution specification Q=80% at 30 minutes.

What is claimed is:

1. A method of treating a disorder selected from dementia, mania or nicotine dependence in a patient in need thereof comprising administering to the patient a tablet comprising as an active ingredient a therapeutically effective amount of galanthamine hydrobromide (1:1) and a pharmaceutically acceptable carrier, wherein said carrier comprises a spray-dried mixture of lactose monohydrate and microcrystalline cellulose (75:25) as a diluent, and an insoluble or poorly soluble cross-linked polymer disintegrant.

2. The method of claim 1 wherein the disorder is dementia.

3. The method of claim 2 wherein the disorder is Alzheimer's dementia.

4. The method of claim 1 wherein the disorder is mania.

5. The method of claim 1 wherein the disorder is nicotine dependence.

6. A fast-dissolving galanthamine hydrobromide (1:1) tablet made by (i) dry blending the active ingredient, an insoluble or poorly soluble cross-linked polymer disintegrant and an optional glidant with a diluent comprising a spray-dried mixture of lactose monohydrate and microcrystalline cellulose (75:25); (ii) optionally mixing a lubricant with the mixture obtained in step (i); (iii) compressing the mixture obtained in step (i) or in step (ii) in the dry state into a tablet; and (iv) optionally film-coating the tablet obtained in step (iii).

\* \* \* \* \*